United States Patent [19]

Yang et al.

[11] Patent Number: 5,773,629

[45] Date of Patent: Jun. 30, 1998

[54] SYNTHESIS OF (4S, 5R) -2, 4-DIPHENYL-5-CARBOXY-OXAZOLINE DERIVATIVE AS TAXOL SIDE-CHAIN PRECURSOR

[75] Inventors: Yuh-Lin Allen Yang, Hsin-Chu Hsien; Ay-Hua Gau, Tai-Tung Hsien, both of Taiwan

[73] Assignee: Industrial Technology Research Institute, Hsinchu, Taiwan

[21] Appl. No.: 663,736

[22] Filed: Jun. 14, 1996

[51] Int. Cl.⁶ .................................................. C07D 263/16
[52] U.S. Cl. ........................................ 548/239; 549/510
[58] Field of Search ............................................ 548/239

[56] References Cited

U.S. PATENT DOCUMENTS

| | | | |
|---|---|---|---|
| 3,741,961 | 6/1973 | Kmiocik | 548/239 |
| 3,813,378 | 5/1974 | Witte et al. | 548/237 |
| 5,128,478 | 7/1992 | Ito | 548/237 |
| 5,476,954 | 12/1995 | Bouezat | 549/310 |
| 5,521,202 | 5/1996 | Yano et al. | 574/369 |

FOREIGN PATENT DOCUMENTS 55-145650  11/1980  Japan .

WO 94-14787  7/1994  WIPO .

OTHER PUBLICATIONS

Gou et al. J. Org Chem vol. 58 pp. 1287–1289, 1993.
Frump, J.A. Chem. Reviews vol. 71 pp. 483–504, 1971.
Wohl et al, J. Org. Chem. vol. 38, No. 10 pp. 1787–1790, 1973.
Oda et al. Bull. Chem. Soc. Jap. vol. 35 pp. 1219–1221, 1962.
Larock et al. Comp. Org. Syn. vol. 4, pp. 292–294, 1991.
Temnikova et al. Chem. Abstr vol. 68 entry 78176 K, 1968.
Smith et al. J. Chem: Soc. Perkin I, pp. 1200–1202, 1975.
Bishop Comp. Org. Syn. vol. 6 pp. 261–300, 1991.
Krimin et al, Org. Reactions, vol. 17, pp. 213–257, 1969.

*Primary Examiner*—Donald G. Daus
*Attorney, Agent, or Firm*—Sughrue, Mion, Zinn, Macpeak & Seas, PLLC

[57] ABSTRACT

The present invention provides a process for preparing a (4S,5R)-2,4-diphenyl-5-carboxy-oxazoline derivative, which can serve as a taxol side-chain precursor, from the treatment of a (2R,3S)-alkyl trans-3-phenyl-2,3-epoxypropionate derivative with benzonitrile in the presence of a strong acid.

15 Claims, No Drawings

SYNTHESIS OF (4S, 5R) -2, 4-DIPHENYL-5-CARBOXY-OXAZOLINE DERIVATIVE AS TAXOL SIDE-CHAIN PRECURSOR

FIELD OF THE INVENTION

The present invention relates to a novel process for the preparation of a (4S,5R)-2,4-diphenyl-5-carboxy-oxazoline derivative, which can be used as a taxol side-chain precursor, from (2R,3S)-alkyl trans-3-phenyl-2,3-epoxypropionate.

DESCRIPTION OF THE PRIOR ART

Early in 1971, taxol having the structure:

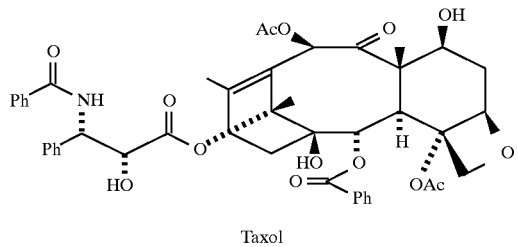

Taxol was isolated from the bark of *Taxus brevifolia* and its chemical structure was determined. After a long period of research and development, taxol has been approved by the U.S. FDA for treating ovarian cancer in December, 1992. Subsequently, taxol has also been approved by many European countries for the treatment of ovarian cancer. Besides, most countries in the world have also approved taxol for the treatment of breast cancer. Clinical tests demonstrate that taxol is also effective for treating lung cancer and other solid tumors.

However, one major drawback of this effective anticancer agent is its extremely limited availability. Since the natural sources of taxol, Taxus species, are slow-growing trees, and only a relatively small amount of taxol is present in these trees, a large number of such trees must be harvested and tedious purification procedures must be used to obtain taxol, thus increasing the cost tremendously.

In recent years, the preparation of taxol by utilizing Baccatin III or 10-deacetylbaccatin III, either of which is present more abundant in other more accessible Taxus species such as *Taxus baccata,* as precursors via a semisynthetic route has been developed. For example, Kingston, et al. (*Tetrahedron Lett.* 1994, 35, 4483–4484) report that taxol can be prepared with a good yield from 7-(triethylsilyl) baccatin III (formula V) (prepared from 10-deacetylbaccatin III) by esterification with (4S,5R)-2,4-diphenyl-5-carboxy-oxazoline (II) (R=H) followed by hydrolysis of the resulting oxazoline ester (VI) with dilute hydrochloric acid. (4S,5R) -2,4-diphenyl-5-carboxy-oxazoline (II) (R=H), serving as a taxol side-chain precursor, can be coupled to the C-13 hydroxy of the baccatin III derivative. After the coupling, the side-chain precursor is then subjected to hydrolysis to open the oxazoline ring and form a taxol side-chain. The process is illustrated by the following reaction Scheme 1:

Scheme 1

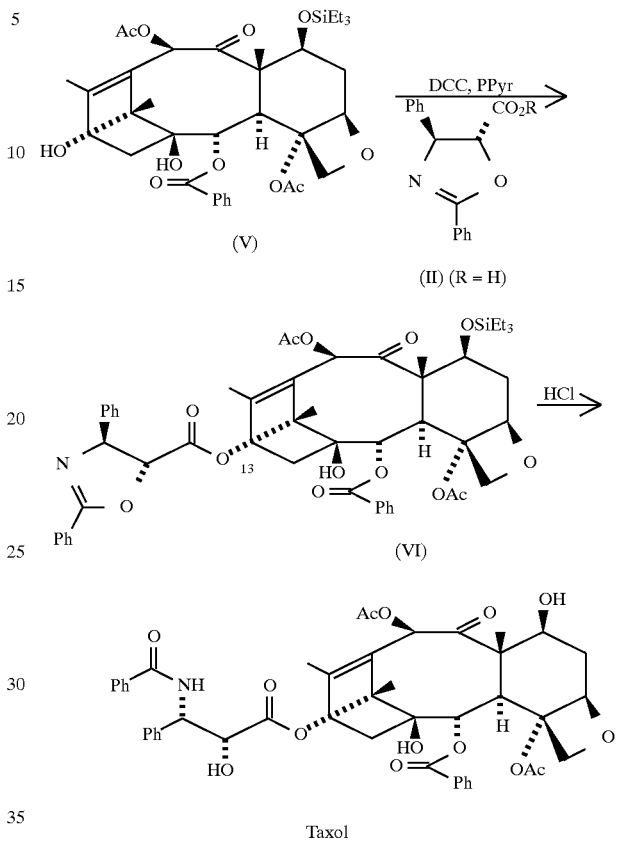

Baccatin III or 10-deacetylbaccatin III required for semi-synthesis of taxol can be obtained from natural plants, however, the taxol side-chain precursor (4S,5R)-2,4-diphenyl-5-carboxy-oxazoline (II) (R=H) still needs to be synthesized.

Many processes for preparing the taxol side-chain precursor (4S,5R)-2,4-diphenyl-5-carboxy-oxazoline (formula II) (R=H) have been proposed. Gou, et al. use several steps and particular reagents to synthesize the taxol side-chain precursor (*J. Org. Chem.* 1993, 58, 1287–1289). However, the yield is not economic at less than 40%, thus wasting the reagents. Poss, et al. (WO 94/14787) provide a process involving the direct cyclization of a taxol side chain compound (VII) to form the taxol side-chain precursor (II)(R=H), which is illustrated in Scheme 2:

Scheme 2

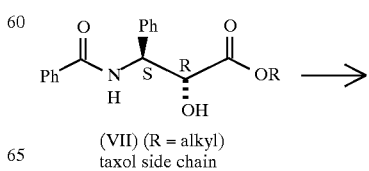

(VII) (R = alkyl)
taxol side chain

-continued
Scheme 2

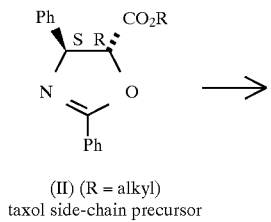

(II) (R = alkyl)
taxol side-chain precursor

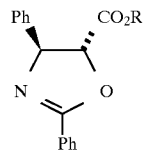

(II) (R = H)

They prepared taxol side-chain derivatives, such as compound (VII) via other tedious routes and used oxazoline ring as protecting function for taxol side-chain to facilitate its coupling with baccatin III derivative.

SUMMARY OF THE INVENTION

An object of the present invention is to provide a novel process for the preparation of an oxazoline derivative of the following formula (II):

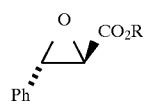

(II)

wherein
Ph is phenyl, and
R is hydrogen,
said process comprising the step of contacting an epoxide derivative of the following formula (I):

$$\underset{Ph}{\overset{O}{\triangle}}CO_2R$$ (I)

wherein
Ph is as defined above, and
R is $C_1$–$C_4$ alkyl,
with benzonitrile in the presence of a strong acid to form an oxazoline derivative of formula (II) (R=$C_1$–$C_4$ alkyl); and subjecting the oxazoline derivative of formula (II) (R=$C_1$–$C_4$ alkyl) to hydrolysis in the presence of a base to form the oxazoline derivative of the formula (II) (R=H).

DETAILED DESCRIPTION OF THE INVENTION

The symbol "Ph" used herein represents "phenyl". The symbol "R", as used herein unless otherwise specified, represents "$C_1$–$C_4$ alkyl."

The overall process for preparing the taxol side-chain precursor can be depicted as the following reaction Scheme 3:

Scheme 3

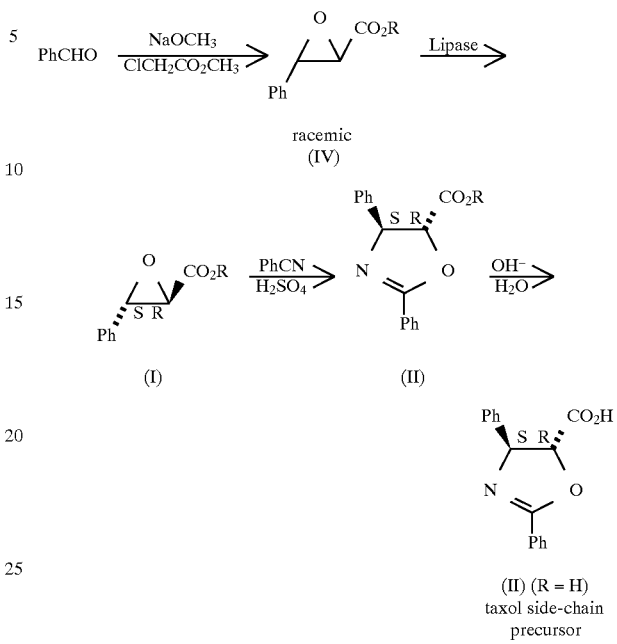

(II) (R = H)
taxol side-chain precursor

Benzaldehyde can be reacted to obtain a racemic trans-3-phenyl-2,3-epoxypropionate derivative (IV) via Darzens condensation reaction, which is then subjected to selective hydrolysis by a lipase to form a chiral (2R,3S)-trans-3-phenyl-2,3-epoxypropionate derivative (I) (R=alkyl). The above two steps have been disclosed in literature (Gou, et al. J. Org. Chem. 1993, 58, 1287–1289).

The novel process of the present invention is to use the epoxide derivative of the formula (I):

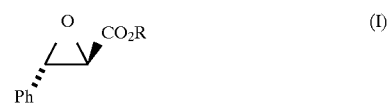

wherein
R is $C_1$–$C_4$ alkyl,
as the starting material to convert to the oxazoline derivative of the formula (II):

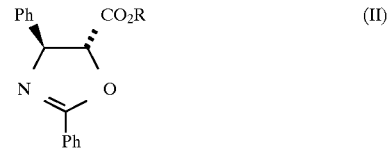

wherein R is $C_1$–$C_4$ alkyl or hydrogen.

Treatment of the epoxide derivative of the formula (I) (R=$C_1$–$C_4$ alkyl) with benzonitrile in the presence of a strong acid can obtain the oxazoline derivative of the formula (II) (R=$C_1$–$C_4$ alkyl) via a Ritter-like reaction. After that, the obtained oxazoline derivative of the formula (II) (R=$C_1$–$C_4$ alkyl) is subjected to hydrolysis in the presence of a base, and the compound of the formula (II) (R=$C_1$–$C_4$ alkyl) can be converted to the compound of the formula (II) (R=H).

The strong acid used in the present process serves as a catalyst for the Ritter-like reaction. In addition to sulfuric acid, other suitable strong acids would include any strong acid suitable for catalyzing a Ritter reaction or a Ritter-like reaction and all the inorganic acids and organic acids listed in Krimen, et al. *Org. React.* 1969, 17, 213–325. Krimen, at page 250, discloses the following acids as useful reagents in the Ritter reaction: perchloric acid, phosphoric acid, polyphosphoric acid, formic acid, substituted sulphonic acids and boron trifluoride. The organic sulfonic acids such as methanesulfonic acid and trifluoromethanesulfonic acid used in a conversion reaction similar to a Ritter reaction disclosed in Senanayake, et al. *Tetrahedron Lett.* 1995, 36, 7615–7618, are also suitable strong acids for use in the present process. In addition, the reaction solvents and reaction temperature ranges described in the above two technical papers are all suitable for application to the present process.

The base used in the present invention is to convert the compound of the formula (II) (R=$C_1$–$C_4$ alkyl) to the compound of the formula (II) (R=H), that is, to hydrolyze the alkoxycarbonyl group (COOR, R=$C_1$–$C_4$ alkyl) of the compound (II) (R=$C_1$–$C_4$ alkyl) to a carboxyl group (COOH). Therefore, all the bases suitable for hydrolysis are suitable for use in the present invention, such as sodium hydroxide, lithium hydroxide and potassium hydroxide.

The Ritter-like conversion reaction, that is, the reaction of converting the compound of formula (I) (R=$C_1$–$C_4$ alkyl) to the compound of formula (II) (R=$C_1$–$C_4$ alkyl), of the present invention is conducted at temperatures between −20° C. and 25° C., preferably between −10° C. and 0° C.

Specifically speaking, according to the present invention, the conversion of the epoxide derivative of the formula (I) via the Ritter-like reaction will afford a mixture of oxazoline derivative stereoisomers including the compound of the formula (II) (R=$C_1$–$C_4$ alkyl) and the compound of the formula (III) (R=$C_1$–$C_4$ alkyl) as shown in Scheme 4.

Scheme 4

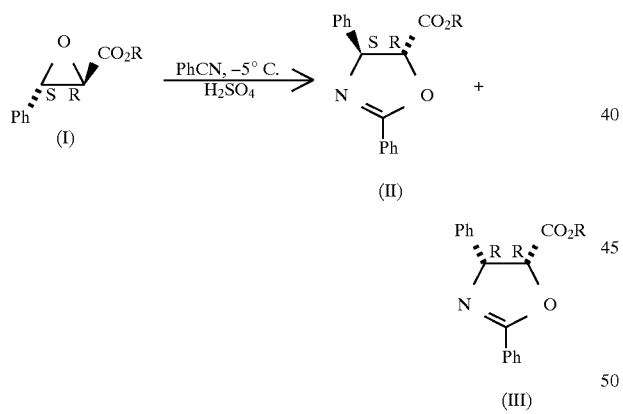

The weight ratio of the compound of the formula (II) (4S,5R) to the compound of formula (III) (4R,5R) is about 3:1.

The obtained two stereoisomers (II) and (III) can be isolated by column chromatography, and the yield of the compound (II) having (4S,5R) form is about 50%. The isolated oxazoline derivative of the formula (II) (R=$C_1$–$C_4$ alkyl) is then subjected to hydrolysis in the presence of a base to obtain (4S,5R)-2,4-diphenyl-5-carboxy-oxazoline, i.e., the compound of the formula (II) (R=H), which can serve as a taxol side-chain precursor for the semisynthesis of taxol.

Alternatively, even more conveniently, (4S,5R)-2,4-diphenyl-5-carboxy-oxazoline can also be obtained by not isolating the stereoisomers of compound (II) and (III) (R=$C_1$–$C_4$ alkyl) prior to hydrolysis. That is to say, the mixture of oxazoline derivative stereoisomers including compound (II) (R=$C_1$–$C_4$ alkyl) and (III) (R=$C_1$–$C_4$ alkyl) is directly subjected to hydrolysis in the presence of a base, then alkoxycarbonyl groups on both of the stereoisomers will be converted to carboxyl groups, and compound (II) (R=H) and (III) (R=H) can be formed. The reaction can be depicted as Scheme 5.

Scheme 5

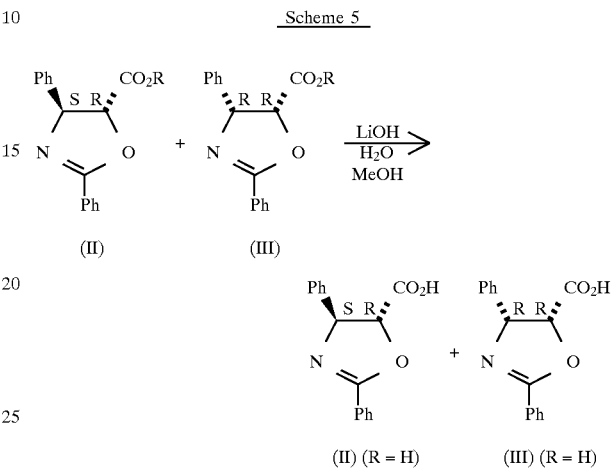

After hydrolysis, the compound of the formula (II) (R=H), the taxol side-chain precursor, can be isolated by precipitation, while another stereoisomer of the formula (III) (R=H) will remain in the solution.

The following examples are intended to demonstrate this invention more fully without limiting its scope, since numerous modifications and variations will be apparent to those skilled in the art.

REFERENTIAL EXAMPLE 1

Preparation of the starting material: (2R,3S)-methyl trans-3-phenyl-2,3-epoxypropionate (I)

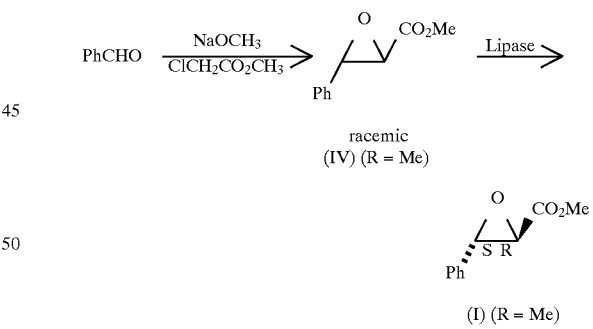

In a reaction vessel cooling in an ice bath under nitrogen atmosphere, sodium methoxide (4.05 g, 75 mmol) was dissolved in dichloromethane with constant stirring. A mixed solution of benzaldehyde (5.3 g, 50 mmol) and methyl 2-chloroacetate (8.15 g, 75 mmol) in dichloromethane was added dropwise in the ice bath. After stirring for 1 hour, the ice bath was removed, and the reaction mixture was stirred for 2 hours at room temperature, then, acetic acid (0.25 ml) and water (50 ml) were added and stirred. The resulting reaction mixture was extracted, washed with brine, dried over anhydrous $MgSO_4$, filtered and concentrated to afford a racemic methyl trans-3-phenyl-2,3-epoxypropionate compound (IV) (R=Me). The racemic compound (IV) was selectively cleaved by a lipase to obtain the chiral compound (I) (R=Me) (ee>98% by HPLC).

The spectroscopic data of compound (I) (R=Me) is as follows:

$^1$H NMR(CDCl$_3$)δ: 3.52 (d, J=1.7 Hz, 1H), 3.83 (s, 3H), 3.10 (d, J=1.75 Hz, 1H), 7.31–7.36 (m, 5H)

Mass (EI), m/e(%): 178(6, M$^+$), 121(100), 91(73), 89(42), 77(19) IR (neat), cm$^{-1}$: 1753, 1459, 1210 Reference: Gou, et al., *J. Org. Chem.* 1993, 58, 1287–1289.

EXAMPLE 1

Preparation of (4S,5R)-2,4-diphenyl-5-(methoxycarbonyl)-oxazoline (II) (R=Me) and (4R,5R)-2,4-diphenyl-5-(methoxycarbonyl)-oxazoline (III) (R=Me)

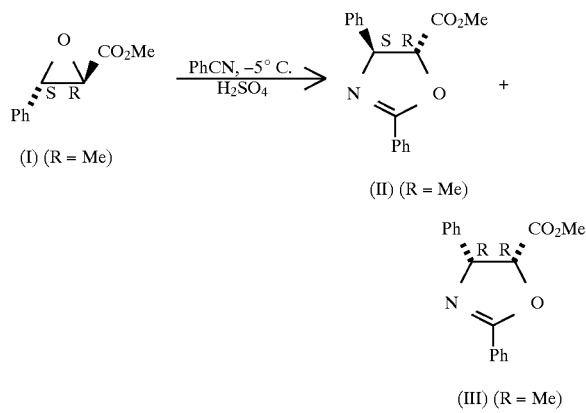

Benzonitrile (1 ml) was charged in a reaction vessel and stirred in salt ice bath (about −5° C. to −7° C.) to which concentrated sulfuric acid (95–97%, 2 ml) was added under nitrogen atmosphere. After stirring for about 10–20 minutes, a mixed solution of the chiral compound (I) (R=Me) (0.43 g, 2.4 mmol) obtained from Referential Example 1 and benzonitrile (0.5 ml) was added slowly and stirred for 1 hour. The reaction mixture was then poured into ice water, neutralized to pH=10 by adding solid sodium carbonate, extracted with ethyl acetate, washed with brine, dried over anhydrous sodium sulfate, filtered, and then concentrated. The crude product was determined by NMR (200 MHz) and found to include compound (II) (R=Me) and compound (III) (R=Me) with a weight ratio of 3:1. Purification of the crude product by silica gel chromatography afforded compound (II) (R=Me) (0.34 g, yield=50%) and a small amount of compound (III) (R=Me).

The spectroscopic data of compound (II) (R=Me) is as follows:

$^1$H NMR(CDCl$_3$)δ: 3.81(s, 3H), 4.87(d, J=6.5 Hz, 1H), 5.41(d, J=6.5 Hz, 1H), 7.29–7.46(m, 8H), 8.03–8.08(m, 2H). Mass (EI), m/e(%): 281(20, M$^+$), 210(29), 105(100), 91(16), 77(63) IR (neat), cm$^{-1}$: 1761, 1742, 1655, 1450, 1064 MP 61°–62° C.

The spectroscopic data of compound (III) (R=Me) is as follows:

$^1$H NMR(CDCl$_3$)δ: 3.20(s, 3H), 5.38(d, J=10.8 Hz, 1H), 5.74(d, J=10.8 Hz, 1H), 7.24–7.52(m, 8H), 8.03–8.13(m, 2H). Mass (EI), m/e(%): 281(4, M$^+$), 222(52), 193(100), 165(18), 89(32), 77(20) IR (neat), cm$^{-1}$: 1761, 1651, 1450, 1211, 1078 MP 138°–139° C.

EXAMPLE 2

Preparation of (4S,5R)-2,4-diphenyl-5-carboxy-oxazoline (II) (R=H)

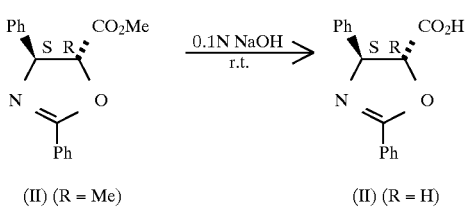

Compound (II) (R=Me) (0.115 g, 0.4 mmol) obtained from Example 1 was placed in a reaction vessel to which was added 0.1N aqueous solution of sodium hydroxide (8 ml, 0.8 mmol). After stirring for 4 hours at room temperature, the reaction mixture was neutralized to pH=2 by adding 1.1N hydrochloric acid, filtered, and dried under reduced pressure to afford solid compound (II) (R=H) (0.083 g, yield=76%).

The spectroscopic data of compound (II) (R=H) is as follows:

$^1$H NMR(CDCl$_3$)δ: 4.97(d, J=6.4 Hz, 1H), 5.48(d, J=6.4 Hz, 1H), 7.38–7.57(m, 8H), 8.04–8.05(m, 2H) Mass (FAB$^+$), m/e(%): 281(100, M$^+$1), 222(4), 147(8), 105(7) IR (neat), cm$^{-1}$: 3375, 1723, 1633, 1495 MP 191°–192° C.

EXAMPLE 3

Preparation of (4S,5R)-2,4-diphenyl-5-carboxy-oxazoline (II) (R=H)

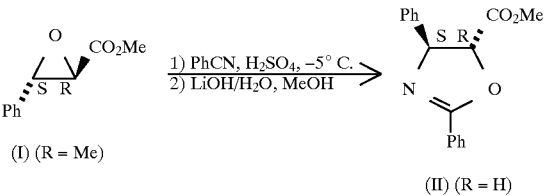

Benzonitrile (1.5 ml) was charged in a reaction vessel and stirred in salt ice bath (about −5° C. to −7° C.) for 10 minutes. Concentrated sulfuric acid (95–97%, 4 ml) was added dropwise under nitrogen atmosphere. After stirring for about 10–20 minutes, a mixed solution of the chiral compound (I) (R=Me) (0.89 g, 5.0 mmol) obtained from Referential Example 1 and benzonitrile (1.5 ml) was added slowly and stirred for 1.5 hour. The reaction mixture was poured into ice water, neutralized to pH=10 by adding solid sodium carbonate, extracted with ethyl acetate, washed with brine, dried over anhydrous sodium sulfate, filtered, and then concentrated. The crude product was chromatographed with a short column to remove benzonitrile and impurities. A mixture of two stereoisomers was obtained (0.83 g).

The above mixture was dissolved in methanol (4 ml) and stirred. Then, lithium hydroxide solution (0.2N, 22 ml) was added slowly. After stirring for 8 hours, the resulting reaction mixture was placed in an ice bath and was adjusted to acidic with 1.1N hydrochloric acid. After stirring for 15 minutes, the solid product was filtered to afford compound (II) (R=H) (0.61 g, yield=50%). The spectroscopic data are the same as listed in Example 2.

What is claimed is:

1. A process for the preparation of an oxazoline compound of the following formula (II):

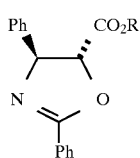

wherein
Ph is phenyl,
and
R is $C_1$–$C_4$ alkyl,
said process comprising the step of contacting an epoxide compound of the following formula (I):

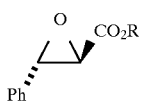

wherein Ph and R are as defined above, with benzonitrile in the presence of a strong acid selected from the group consisting of sulfuric acid, perchloric acid, phosphoric acid, polyphosphoric acid, formic acid, boron trifluoride, methanesulfonic acid, and trifluoromethanesulfonic acid to form said oxazoline compound of the formula (II).

2. The process as claimed in claim 1, wherein the strong acid is selected from the group consisting of sulfuric acid, methanesulfonic acid and trifluoromethanesulfonic acid.

3. The process as claimed in claim 1, wherein the process is conducted at temperature between –20° C. and 25° C.

4. The process as claimed in claim 3, wherein the process is conducted at temperature between –10° C. and 0° C.

5. A process for the preparation of an oxazoline compound of the following formula (II):

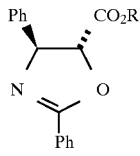

wherein
Ph is phenyl, and
R is hydrogen,
said process comprising the steps of:
(a) contacting an epoxide compound of the following formula (I):

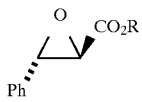

wherein
Ph is as defined above, and
R is $C_1$–$C_4$ alkyl,
with benzonitrile in the presence of a strong acid selected from the group consisting of sulfuric acid, perchloric acid, phosphoric acid, polyphosphoric acid, formic acid, boron trifluoride, methanesulfonic acid, and trifluoromethanesulfonic acid to form a mixture of oxazoline derivative stereoisomers including an oxazoline compound of the formula (II) where R=$C_1$–$C_4$ alkyl;
(b) isolating the oxazoline compound of the formula (II) where R=$C_1$–$C_4$ alkyl; and
(c) subjecting the oxazoline compound of the formula (II) where R=$C_1$–$C_4$ alkyl to hydrolysis in the presence of a base capable of hydrolyzing the alkoxycarbonyl group (COOR, R=$C_1$ to $C_4$ alkyl) of the compound (II) (where R=$C_1$ to $C_4$ alkyl) to a carboxyl group (COOH) to form said oxazoline compound of the formula (II) where R=H.

6. The process as claimed in claim 5, wherein the strong acid is selected from the group consisting of sulfuric acid, methanesulfonic acid and trifluoromethanesulfonic acid.

7. The process as claimed in claim 5, wherein the step (a) is conducted at temperature between –20° C. and 25° C.

8. The process as claimed in claim 7, wherein the step (a) is conducted at temperature between –10° C. and 0° C.

9. The process as claimed in claim 5, wherein the base is selected from the group consisting of sodium hydroxide, lithium hydroxide and potassium hydroxide.

10. A process for the preparation of an oxazoline compound of the following formula (II):

wherein
Ph is phenyl, and
R is hydrogen,
said process comprising the steps of:
(a) contacting an epoxide compound of the following formula (I):

wherein
Ph is as defined above, and
R is $C_1$–$C_4$ alkyl,
with benzonitrile in the presence of a strong acid selected from the group consisting of sulfuric acid, perchloric acid, phosphoric acid, polyphosphoric acid, formic acid, boron trifluoride, methanesulfonic acid, and trifluoromethanesulfonic acid to form a mixture of oxazoline compound stereoisomers including an oxazoline compound of the formula (II) where R=$C_1$–$C_4$ alkyl;
(b) subjecting the mixture of oxazoline compound stereoisomers to hydrolysis in the presence of a base capable of hydrolyzing the alkoxycarbonyl group (COOR. R=$C_1$ to $C_4$ alkyl) of the compound (II) (where R=$C_1$ to $C_4$ alkyl) to a carboxyl group (COOH) without isolating the oxazoline compound of the formula (II) where R=$C_1$–$C_4$ alkyl prior to the hydrolysis; and
(c) isolating the oxazoline compound of the formula (II) where R=H.

11. The process as claimed in claim 10, wherein the strong acid is selected from the group consisting of sulfuric acid, methanesulfonic acid and trifluoromethanesulfonic acid.

12. The process as claimed in claim 10, wherein the step (a) is conducted at temperature between –20° C. and 25° C.

13. The process as claimed in claim 12, wherein the step (a) is conducted at temperature between –10° C. and 0° C.

14. The process as claimed in claim 10, wherein the base is selected from the group consisting of sodium hydroxide, lithium hydroxide and potassium hydroxide.

15. The process as claimed in claim 10, wherein in step (c), the oxazoline compound of the formula (II) (R=H) is isolated by precipitation.

* * * * *